United States Patent
Hunt (10) Patent No.: US 7,811,831 B2
(45) Date of Patent: Oct. 12, 2010

(54) SYSTEMS AND METHODS FOR MOLECULAR RECOGNITION

(75) Inventor: William D. Hunt, Decatur, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 392 days.

(21) Appl. No.: 11/809,502

(22) Filed: Jun. 1, 2007

(65) Prior Publication Data

US 2008/0108150 A1     May 8, 2008

Related U.S. Application Data

(62) Division of application No. 10/863,150, filed on Jun. 7, 2004, now Pat. No. 7,413,892.

(60) Provisional application No. 60/476,103, filed on Jun. 5, 2003.

(51) Int. Cl.
*G01N 33/552* (2006.01)

(52) U.S. Cl. .................. 436/527; 436/524; 436/815; 436/901

(58) Field of Classification Search ........... None
See application file for complete search history.

(56) References Cited

U.S. PATENT DOCUMENTS

| 4,735,906 A | | 4/1988 | Bastiaans |
| 5,179,028 A | * | 1/1993 | Vali et al. .................. 436/524 |
| 5,770,389 A | * | 6/1998 | Ching et al. .............. 435/7.92 |

OTHER PUBLICATIONS

Ngeh-Ngwainbi et al, "Parathion Antibodies on Piezoelectric Crystals", J. Am. Chem. Soc., 1986, 108, 5444-5447.*

* cited by examiner

*Primary Examiner*—Christopher L Chin
(74) *Attorney, Agent, or Firm*—Perkins Coie LLP (57) ABSTRACT

Acoustic wave devices coated with a biolayer are described for the detection target bio-molecules. The acoustic wave device is connected in an oscillator circuit, and the frequency shift $\Delta f$ resulting from a biomolecular event is recorded. Further described are the use of Rayleigh wave surface acoustic wave devices for vapor phase detection as well as quartz crystal microbalance devices for liquid phase measurements. A biofilm on the surface of the acoustic wave device comprises of a layer of antibodies raised against a specific target molecule or antigen. Signatures for detection events are presented in the form of frequency shifts $\Delta f(t)$.

8 Claims, 6 Drawing Sheets

SYSTEMS AND METHODS FOR MOLECULAR RECOGNITION

CROSS-REFERENCE TO RELATED APPLICATIONS

This application is a divisional application of U.S. application Ser. No. 10/863,150, filed Jun. 7, 2004, now U.S. Pat. No. 7,413,892, which application claims priority to U.S. Provisional Patent Application No. 60/476,103 filed Jun. 5, 2003, which applications are hereby incorporated by reference in their entirety.

TECHNICAL FIELD

The invention concerns acoustic wave sensors. More specifically, the invention relates to the detection of biochemical materials by use of acoustic wave detection.

BACKGROUND

The highly specific and complex nature of olfactory sensing systems has inspired researchers to develop vapor phase chemical detection systems, commonly referred to as "electronic noses." These devices and systems are currently being used in biotechnology, as well as applications in medicine, the environment, the food industry, and most recently law enforcement applications. Interdiction efforts continue in the search for technologies which can provide an inexpensive alternative to dogs as detectors of narcotics and explosives. One of the principal motivations for the development of electronic noses for such applications is the expense associated with the handling, training, and care of such dogs, Furthermore, it is often unclear what chemicals the dogs are actually detecting, and response vary considerably amongst dogs. As an example, not all dogs do respond to the same cocaine sample. Although the dogs have proved to be a highly useful tool in detecting illicit materials, they have inherent limitations in reliability, as one would never accept data from an instrument without having a solid idea of the physical mechanism behind a detection event.

Acoustic sensors represent a long-standing an approach for high-precision sensing. Quartz crystal microbalances (QCMs) have been utilized since the 1950s to monitor the thickness of metals being deposited on wafers in evaporation systems. Such sensors have leveraged investments in other technologies, namely, oscillator designs and electronic frequency counters. In addition, the investments in frequency control and radar during World War II and for the quarter century that followed led to a detailed understanding of the temperature characteristics of quartz, largely at the Ft. Monmouth, N.J., Army Research Lab in the United States. In cuts of quartz such as the AT-cut used for QCM, the linear expansion of the material with increasing temperature is compensated by an increase in the acoustic velocity such that the round trip delay for an acoustic wave in a resonator does not vary with temperature. However, current implementations of QCMs, as used to detect chemicals in the liquid phase, suffer from the inability to distinguish molecular detection events from noise, such as the binding of extraneous substances to the detection device. Furthermore, existing models of recognition events are static, and do not account for time variations in the state of detection devices, and thereby ignore important distinguishing characteristics of detection events. One such static model is the Sauerbrey equation, i.e.,:

$$\Delta \Box f = -\frac{2 f_o^2 \rho_s}{V_a \rho_r}$$

where $\Delta f$ is the resonator frequency shift; $f_o$ is the resonator center frequency; $\rho_s$ is the mass density per $m^2$ of analyte attached to the surface; $V_a$ is the acoustic wave velocity in the resonator, and $\rho_r$ is the volume mass density of resonator material. (further described in "Use of quartz vibrator for weighing thin films on a microbalance," Z Phys., vol. 155, pp. 206-210, 1959.). By failing to account for changes in response over time, such models are often inadequate to distinguish molecular recognition events from noise.

Acoustic wave "biosensors" are distinguished from chemical sensors in that they use a molecule of biological origin (e.g., antibody, cell, enzyme, protein) immobilized onto a surface as the chemically sensitive film on a device. In the prior art, the detection of the presence of entities of biological origin, such as proteins or cells, has taken place in liquids as a requirement. Accordingly, there is a need for an acoustic sensor and models for signature recognition which have one or more of the following features: (1) allow for the detection of targets other than bio-molecules, (2) do not limit the detection environment to the liquid phase; (3) allow detection of bio-molecules in the vapor phase; (4) allow for the detection of molecular recognition events through time-dependent signatures, to improve accuracy and speed of detection.

SUMMARY

The invention includes acoustic wave biosensors that utilize bio-molecules to achieve molecular recognition in the vapor phase and liquid phase as well. The techniques described herein for detection of analytes in the vapor phase may be used to recognize the presence of various airborne analytes that may be of interest, including small molecules such as cocaine; many examples of such airborne analytes shall be readily apparent to those skilled in the art. In non-limiting embodiments of the invention, monoclonal antibodies are used for the molecular recognition; non-limiting examples of such monoclonal antibodies include IgG monoclonal antibodies. In embodiments of the invention, antibodies specific for a target antigen are utilized as a chemically specific receptor molecule. Embodiments of the invention include a database of signatures of responses that are related to a molecular recognition event between antibody and antigen. These signatures may include frequency shifts, recorded before, during, and after binding events (i.e., a binding of an antigen to the antibody), which are used to identify the occurrence of a binding event. Further embodiments include methods for evaluation of such signatures, through models based on time-dependent perturbation theory. Embodiments of the invention also enable the recognition of target molecules in liquid samples by exposing samples which may have the target molecule to an active sensor, while exposing reference samples of the liquid known not to contain the target to a reference sensor. In some embodiments, the active sensor and reference sensor may be physically proximate, and otherwise identically disposed. In some such embodiments, a frequency plot may be monitored, which subtracts a resonance frequency of the reference sensor from that of the active sensor, in order to detect signature changes in frequency characteristic of the presence of the target molecule at the active sensor. These and other embodiments are described more particularly herein.

DETAILED DESCRIPTION

A. Introduction

The following description presents many examples of vapor and liquid phase acoustic wave biosensors, as well as the signatures of responses that are related to molecular recognition that are related to molecular recognition events between antibodies and antigens. Methods are also described for evaluation of such signatures. The embodiments and examples described herein are for illustrative purposes only; many modifications, variations, and equivalents shall be readily apparent to those skilled in the art. In particular, signatures are described herein for the vapor phase detection of small molecules, examples of which are uranine and cocaine. Other examples are presented for the detection of small and large molecules in the liquid phase. These examples are presented for illustrative purposes only, and many examples of molecules detectable by the invention shall be apparent to those skilled in the art.

B. Detection Method and Apparatus

Figure 2:
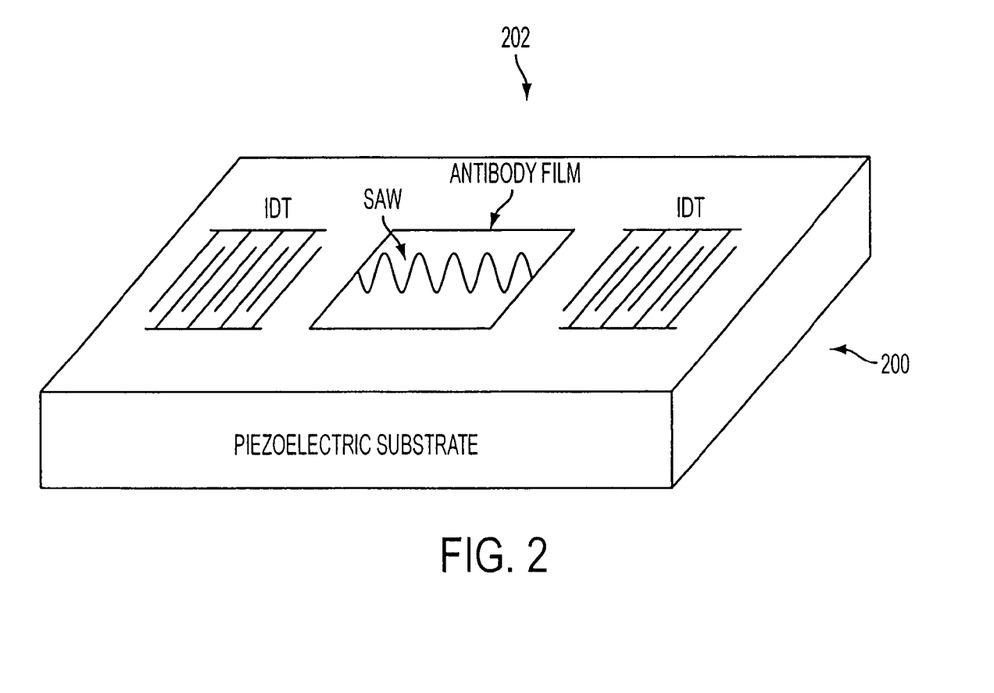
FIG. 2 illustrates a delay-line form of a Surface Acoustic Wave detector, configured in accordance with embodiments of the invention.

Embodiments of the invention include an apparatus for the detection of bio-molecules, as schematically depicted in FIG. 2 200, which includes an acoustic wave device 200 coated with a layer of biological material, or bio-layer 202. In embodiments of the invention, the acoustic wave device 200 is connected to an oscillator circuit, such that a frequency shift resulting from a bio-molecular event may be recorded; this frequency shift may be compared to a signature for a known bio-molecular event, in order to detect/distinguish the bio-molecular event. The bio-layer 202, which is disposed on a surface of the acoustic wave detector 200 may include a layer of anti-bodies responsive to a specific target molecule, or antigen.

Embodiments of the invention allow for detection of bio-molecules in vapor phase or liquid phase. In some embodiments, a Rayleigh wave surface acoustic wave device may be used for vapor phase detection. In embodiments, quartz crystal microbalance (QCM) devices may be used of liquid phase measurements.

C. Detection of Small Molecules

1. Example of Vapor Phase Detection—Uranine

Figure 1:
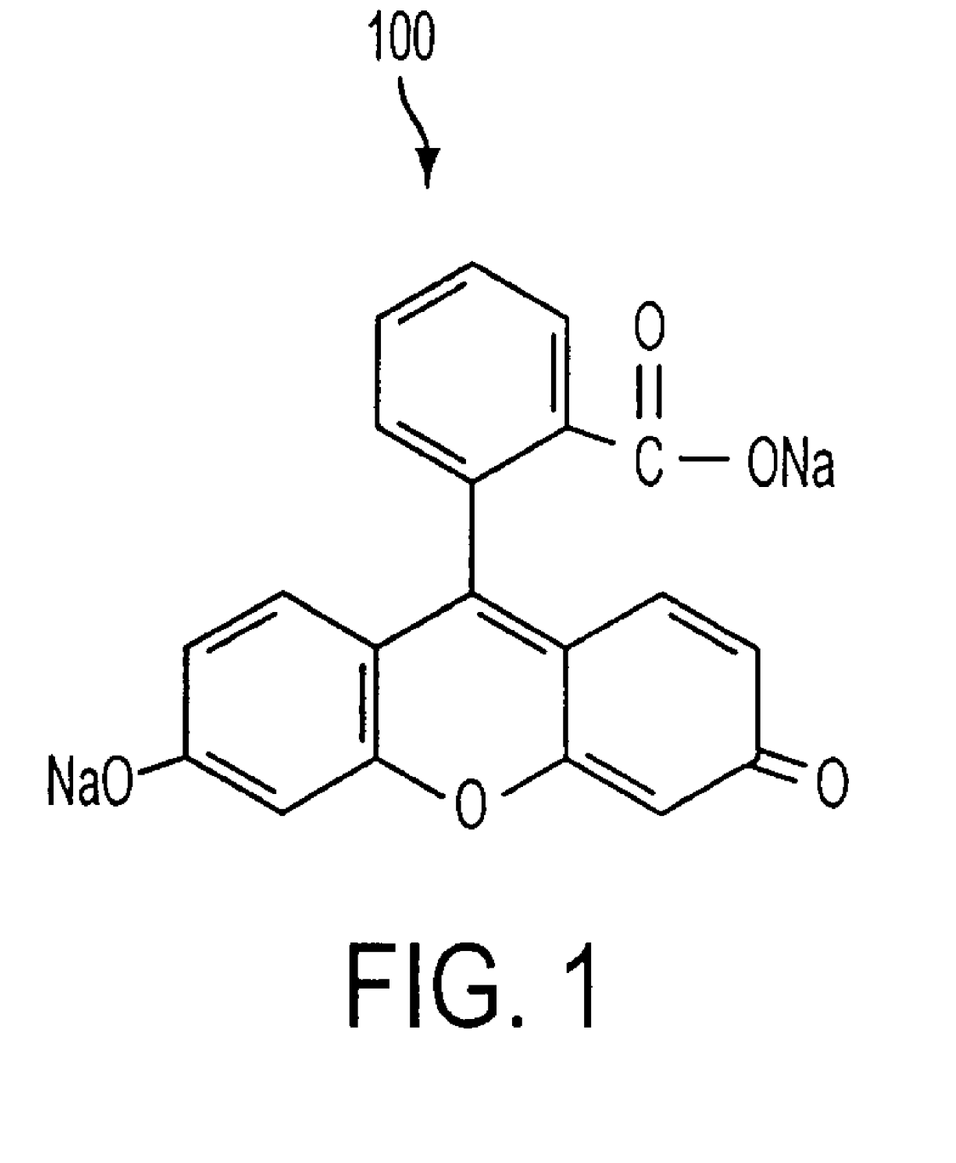
FIG. 1 illustrates structural formulas of examples of substances detectable by embodiments of the invention.

As a non-limiting, illustrative example of vapor phase detection of small molecules, described herein is a method for detection of uranine (fluorescein sodium salt); the chemical structure 100 of which is depicted in FIG. 1. The fluorescence of uranine may be used to provide independent confirmation of the occurrence of binding events with the antibody film 202 coated on the device, which are otherwise detected by the signature recognition techniques of the invention. Embodiments of the invention utilize a vapor phase biosensor by immobilizing a monolayer of antibodies 202 onto the surface of a 250-MHz SAW device fabricated on ST-Quartz. In some such embodiments, the monolayer of antibodies may include anti-FITC antibodies. For the particular cut and propagation direction, the interdigitated transducer on the device generates a Rayleigh which has particle polarization in the saggital plane that is retrograde and decays within roughly one acoustic wavelength from the surface. Such Surface Acoustic Wave (SAW) devices may obtain sensitivities of approximately 20 Hz/pg with a detection limit on the order of a few picograms. To illustrate the sensing mechanism, as a non-limiting example a simple version of this device structure, a SAW delay line, is schematically illustrated in FIG. 2. This device may be connected into an oscillator circuit, allowing the frequency of oscillation can be measured with great precision. In embodiments of the invention, the SAW device and the oscillator circuit may share a physical housing. Other alternative form factors shall be readily apparent to those skilled in the art.

In the example of a SAW delay line, when the antigen binds to the antibody, the acoustic velocity is decreased, and the oscillator frequency shifts to a lower value. In alternative embodiments, a SAW resonator may be used. In such embodiments, because a binding event might take place in either the reflector gratings or the transducer sections of the device, the frequency can increase or decrease in the presence of a binding event. Furthermore, while stiffness changes in the biofilm would increase the resonant frequency of a delay line SAW sensor, they may increase or decrease the frequency of a SAW resonator.

Figure 3:
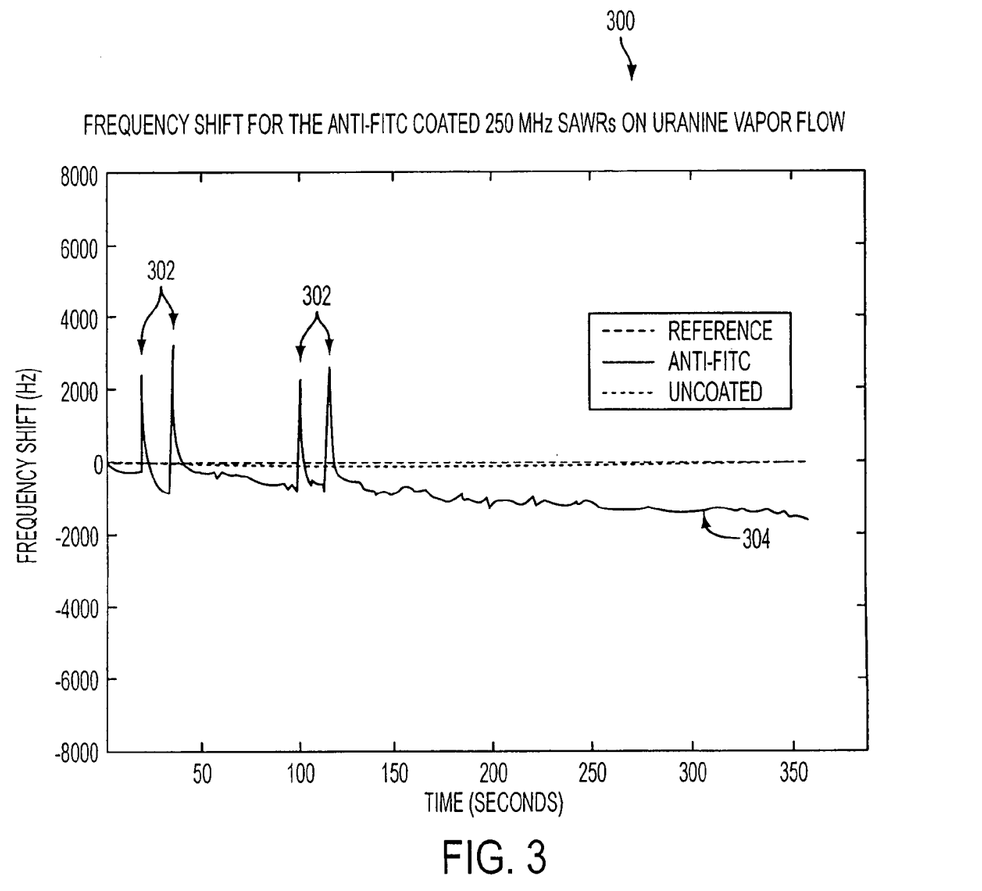
FIG. 3 illustrates a response of the Surface Acoustic Wave detector to target molecules, in accordance with embodiments of the invention.

FIG. 3 illustrates SAW resonator responses 300 to the introduction of uranine vapor past the SAW resonator device. In the depicted response 300, the response of a reference device and oscillator circuit taken simultaneously with the response from the coated SAW resonators has already been subtracted from the recorded responses presented. These reference device has been subjected to the same temperature environment as the sensor under test, but is not exposed to the analyte stream. The sensor data shown in FIG. 3 have already had the reference variation subtracted out; this resultant frequency shift was measured and recorded. Antigen-antibody binding for the uranine vapor and the anti-FITC antibody film is shown to have occurred quickly through frequency shifts 302. In FIG. 3, we present the response of an anti-FITC coated device and an uncoated device to uranine vapor. The anti-FITC coated device shows a radical frequency response 302 and a fairly substantial shift in the baseline frequency 304. This permanent shift in the baseline frequency represents direct evidence of molecular recognition in the vapor phase.

2. Example of Vapor Phase Detection—Cocaine

Figure 4:
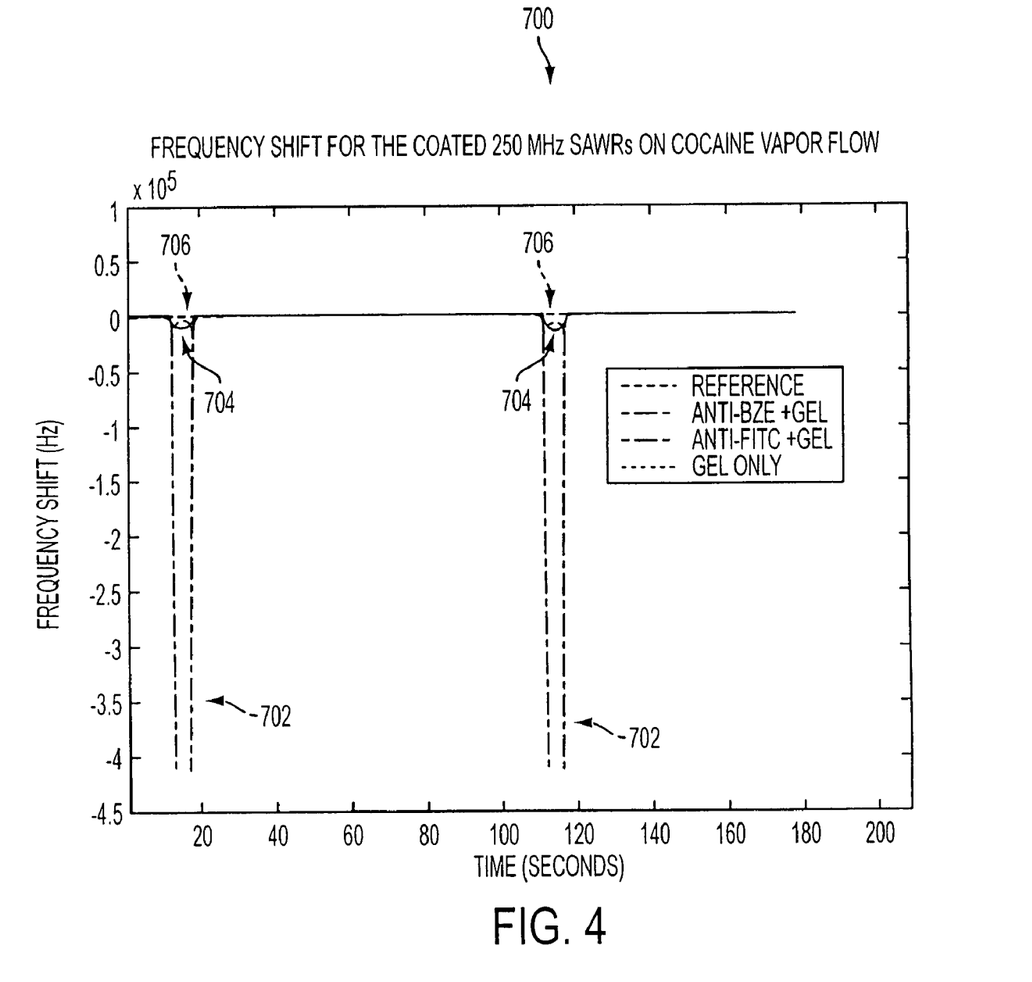
FIG. 4 illustrates a response of a device configured to identify substances in vapor form, in accordance with embodiments of the invention.

In non-limiting embodiments of the invention, immobilized antibodies for benzoylecgonine (BZE) 202 are used as the antibody film for positive detection of cocaine. FIG. 4 presents 700 the response of anti-FITC, anti-BZE, and hydrogel-only sensors to a 1-ng pulse of cocaine over 5-s intervals. The pulse was injected into a constant flow of 180 cubic centimeters per minute (ccm) to minimize the impact associated with a sudden pressure differential. The anti-BZE device 702 has a far more dramatic instantaneous response than the anti-FITC device 704. Note also that there is little or no difference between the gel-only 706 and anti-FITC 704 device responses. This characteristic response is independent of the SAW resonator device location within the sensor head which holds and facilitates the simultaneous sampling of four sensors. During the pulse cycles, a consistent relationship obtains between the sequence and the amount of frequency shift (Δf) on the presentation of cocaine vapor. In short, the magnitude of the frequency shifts can be depicted as follows:

Δf (during pulse cycle): Uncoated<Gel only<Anti-FITC/gel<<Anti-BZE/gel

These differences in the magnitude of the frequency shift between anti-BZE and other sensors are utilized, according to embodiments of the invention, for the establishment of a decision criterion for the real time cocaine detection.

3. Liquid Phase Detection of Small Molecules

Embodiments of the invention enable the detection of small molecules in the liquid phase. As an illustrative example, a QCM device, such as a 10-MHz commercially available QCM, may be used as the SAW device. Other suitable SAW devices shall be apparent to those skilled in the art.

In embodiments of the invention, detection of the target molecule is performed by use of a active sensor and a reference sensor; in some such embodiments, the active and reference sensors are physically proximate, such that that the only significant difference between the active sensor and passive sensor is that the molecular recognition event, i.e., the binding of the target molecule to the immobilized antibodies, occurs on the active sensor and does not occur on the reference sensor. Accordingly, a difference in resonant frequencies between the two sensors is indicative of the molecular recognition event. In embodiments of the invention, resonant frequency changes may be monitored in real-time, and in particular, before, during, and after the molecular recognition event. This upward shift may be used as a signature to detect the occurrence of the molecular recognition event, and distinguish it from any noise, including noise caused by the adhesion of non-targeted biological materials to the reference and sensor.

Figure 5:
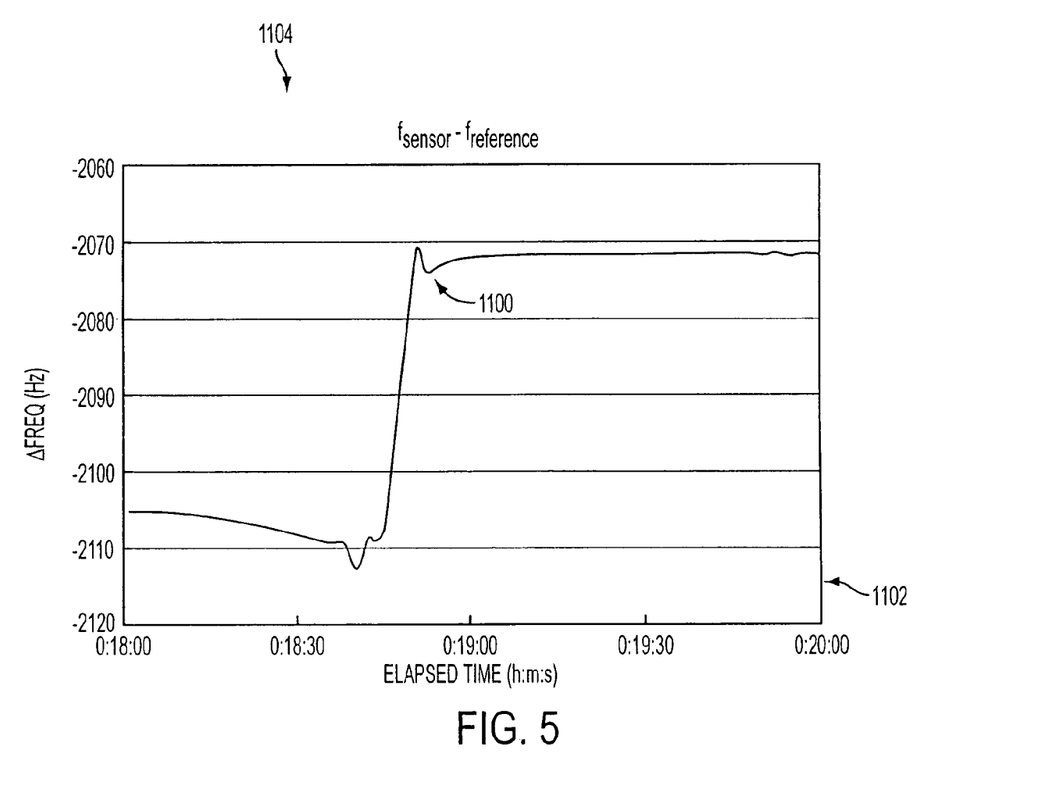
FIG. 5 illustrates a response of a sensor to a substance identified in a liquid phase, in accordance with embodiments of the invention.

As an illustrative, non-limiting example, the use of the a dual sensor detection device is described herein as used to detect a biological molecule in a liquid phase; in this example, the dual sensor detection device is used to detect increasing concentrations of uranine in blood sera. The resonant frequency response 1100 of the detection event is presented in FIG. 6, in which the x-axis 1102 plots the elapsed time, and the y-axis 1104 shows the resonant frequency of the reference is subtracted from the reference frequency of the sensor. As illustrated in FIG. 5, the molecular recognition event 110 corresponds to an upward shift in the frequency of the of the active sensor 1104.

The response in FIG. 5 was obtained from the CM as 100 μl of a nanomolar solution of uranine was added to a 4:3(v/v) mixture of serum to Tris-acetate/EDTA (TAE) buffer. The reference crystal was prepared in the same fashion as the anti-uranine coated sensor, which used an alkane-thiol attachment protocol. Both sensors were fitted to a flow cell that allowed only one side of each crystal to be exposed to the liquid. Careful addition of 100 μl of 1-nM concentration of uranine followed by monitoring of the initial transient and subsequent frequency change was recorded and a sample transient curve is presented in FIG. 5. This concentration, diluted from the nanomolar uranine, corresponds to a detection limit of less than 1 ppb, and this in the presence of perhaps thousands of complex proteins contained in the blood sera. This implementation is presented for illustrative purposes only; many alternative implementations shall be readily apparent to those skilled in the art.

a. Detection of Proteins

Figure 6:
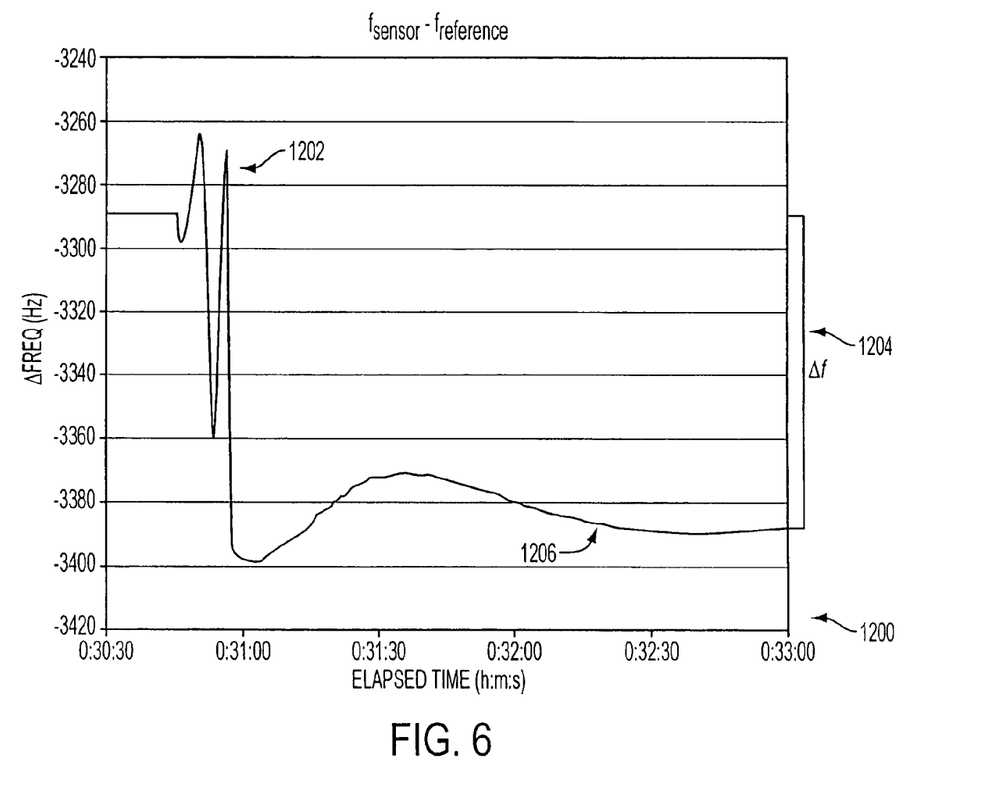
FIG. 6 illustrates a response of a sensor device to an example protein, in accordance with embodiments of the invention.

Embodiments of the invention enable the detection of target proteins. As an illustrative, non-limiting example, described herein is an application of the invention to detect the calmodulin, a plant protein significant for its role as a biomarker in embryonic development of seedlings; as will be apparent to those skilled in the art, the invention may be applied to a variety of target proteins In this example, the active sensor has an anti-calmodulin antibody immobilized on the surface, with 100 μl of 5 μg/ml calmodulin added to the TAE buffered solution. This represents the introduction of 500 ng of calmodulin into the reservoir. The resulting transient QCM response 1200 is shown in FIG. 6, by a downward shift in frequency. Other distinguishing features in the signature 1206 include overshoot and ringing followed by an asymptotic approach to a baseline shifted by a factor Δf 1204.

D. Models of Signatures for Binding Events

Embodiments of the invention include models for binding events in the acoustic wave sensor devices 200, which are time-dependent, and accordingly constitute alternatives to the standard Sauerbrey equation. In some such models, the change in the resonant frequency Δω(t) is related to a change in the stiffness of the immobilized antibody film Δμ(t). One such example is presented by the following equation:

$$\Delta\omega = \frac{1}{t}\left(\int \frac{\omega_u h_f}{\pi\sqrt{\rho_q \mu_q}}\left\{-\omega\left[\Delta\rho(\tau) - \frac{\Delta\mu(\tau)}{V_s^2}\right]\right\}d\tau + i\left[\Delta\rho(t) - \frac{\Delta\mu(t)}{V_s^2}\right] + C\right)$$

where C is a constant to be utilized in satisfying the initial condition of a problem.

E. Conclusion

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A method of detecting a biological material in a vaporous sample, the method comprising:
    exposing the vaporous sample to a coated surface of a surface acoustic wave resonator, the coated surface including an immobilized antibody that is antigenic to the biological material, wherein the surface acoustic wave resonator is in communication with an oscillator circuit that monitors in real-time, based on time-dependent perturbation theory, a surface acoustic waveform produced by the surface acoustic wave resonator;
    after exposing the biological material to the coated surface, detecting presence of the biological material in the vaporous sample, detecting the presence of the biological material further including detecting, using the oscillator circuit, a change in a signature of the surface acoustic waveform of the coated material, and comparing this signature-change in the surface acoustic waveform to a reference signature-change indicative of the presence of the biological material.

2. The method of claim 1, wherein the immobilized antibody is a monoclonal antibody.

3. The method of claim 2, wherein the monoclonal antibody is an IgG monoclonal antibody.

4. The method of claim 1, wherein the reference signature-change is selected from a database including a plurality of reference signature-changes indicative of the presence of a plurality of biological materials.

5. The method of claim 1, wherein the biological material includes a form of cocaine.

6. The method of claim 5, wherein the immobilized antibody includes an antibody for benzoylecgonine.

7. The method of claim 1, wherein the signature-change in the surface acoustic waveform includes a change in a frequency of the surface acoustic waveform.

8. The method of claim 7, further including:
prior to comparing the signature-change in the surface acoustic waveform, subtracting a baseline waveform from the surface acoustic waveform after the exposure of the biological material, wherein the baseline waveform is characteristic of the coated surface when unbound from the biological material.

* * * * *